United States Patent
Bhairam

(10) Patent No.: US 9,565,865 B2
(45) Date of Patent: Feb. 14, 2017

(54) METHOD FOR MAKING COFFEE PRODUCTS CONTAINING CANNABIS INGREDIENTS

(71) Applicant: Imbue LLC, Garden City, NY (US)

(72) Inventor: Christopher Bhairam, Garden City, NY (US)

(73) Assignee: Imbue LLC, Garden City, NY (US)

( * ) Notice: Subject to any disclaimer, the term of this patent is extended or adjusted under 35 U.S.C. 154(b) by 0 days.

(21) Appl. No.: 14/819,830

(22) Filed: Aug. 6, 2015

(65) Prior Publication Data

US 2016/0044934 A1 Feb. 18, 2016

Related U.S. Application Data

(60) Provisional application No. 62/037,827, filed on Aug. 15, 2014.

(51) Int. Cl.
| | | |
|---|---|---|
| *A01N 65/00* | (2009.01) | |
| *A23F 5/14* | (2006.01) | |
| *A61K 36/185* | (2006.01) | |
| *A61K 31/352* | (2006.01) | |
| *B01D 11/02* | (2006.01) | |
| *A23F 5/26* | (2006.01) | |
| *A61K 31/00* | (2006.01) | |

(52) U.S. Cl.
CPC . *A23F 5/14* (2013.01); *A23F 5/26* (2013.01); *A61K 31/00* (2013.01); *A61K 31/352* (2013.01); *A61K 36/185* (2013.01); *B01D 11/02* (2013.01); *B01D 11/0288* (2013.01); *A61K 2236/00* (2013.01)

(58) Field of Classification Search
CPC ..................................... A61K 36/00
USPC ........................................ 424/725
See application file for complete search history.

(56) References Cited

U.S. PATENT DOCUMENTS

| | | |
|---|---|---|
| 6,630,507 B1 | 10/2003 | Hampson et al. |
| 6,759,072 B1 | 7/2004 | Gutwein et al. |
| 7,438,941 B2 | 10/2008 | Gutwein et al. |
| 8,336,186 B2 | 12/2012 | Bloome et al. |
| 8,481,091 B2 | 7/2013 | Ross |
| 8,586,117 B2 | 11/2013 | Vastardis et al. |
| 8,720,320 B1 | 5/2014 | Rivera |
| 2004/0049059 A1 | 3/2004 | Mueller |
| 2015/0352044 A1 | 12/2015 | Benson et al. |

OTHER PUBLICATIONS

Website link: http://en.wikipedia.org/wiki/Tea—The article is about the beverage, Tea (27 pages).
Website link: http://www.potocoffee.coffee/products (1 page).
Website link: http://www.ganjagrindz.com/products--reviews.html (1 page).
Website link: http://www.houseofjane.com/ (1 page).
Website link: http://fairwindscannabis.com/catapult-coffee/ (1 page).
Website link: http://kushcups.com/details/ (1 page).
Website link: http://www.lordandsterling.com/ (1 page).

*Primary Examiner* — Michael Meller
(74) *Attorney, Agent, or Firm* — Locke Lord LLP; Peter J. Fallon

(57) ABSTRACT

The present disclosure is directed to methods of making a coffee products containing cannabinoids that are extracted from *Cannabis* plant. According to one embodiment, the method includes the steps of (a) extracting cannabinoids from *Cannabis* plant; and (b) admixing the cannabinoids into a coffee product. The disclosed methods produce coffee products that possesses the benefits of both coffee and *Cannabis* plant. The methods can be used to produce different coffee products including single-serve coffee pods, ground coffee, and espresso. The methods are used to make coffee products with desired and consistent amount of tetrahydrocannabinol (THC).

18 Claims, 2 Drawing Sheets

METHOD FOR MAKING COFFEE PRODUCTS CONTAINING CANNABIS INGREDIENTS

The present application is related to U.S. Provisional Patent Application No. 62/037,827, filed Aug. 15, 2014, entitled "METHOD FOR MAKING COFFEE PRODUCTS CONTAINING CANNABIS INGREDIENTS." The present application hereby claims priority under 35 U.S.C. .sctn.119(e) to U.S. Provisional Patent Application No. 61/270,897 and is hereby incorporated by reference into the present application as if fully set forth herein.

BACKGROUND

In light of marijuana legalization in multiple states, the use of *Cannabis* plant and its psychoactive ingredients, i.e., cannabinoids, in various foods and beverages, for example, coffee drinks, now becomes feasible.

The invention disclosed and taught herein generally relates to the method for making coffee products containing *Cannabis* ingredients. In particular, methods for making coffee products mixed with extractions of *Cannabis* concentrates.

Cannabinoid compounds are concentrated in a viscous resin produced in structures known as glandular trichomes of the *Cannabis* plant. At least 85 different cannabinoids have been isolated from the *Cannabis* plant, and some of the more studied cannabinoids include tetrahydrocannabinol (THC), cannabidiol (CBD), and cannabinol (CBN). THC is the primary psychoactive component of the *Cannabis* plant.

There are two major species of *Cannabis*, *Cannabis Sativa* and *Cannabis Indica*. *Cannabis Sativa* has a higher level of THC compared to CBD, while *Cannabis Indica* has a higher level of CBD compared to THC. It has been postulated that *Cannabis* strains with relatively high CBD:THC ratios are less likely to induce anxiety than relatively high ratios of THC:CBD. This may be due to CBD's antagonistic effects at the cannabinoid receptors, compared to THC's partial agonist effect. This likely means the high concentrations of CBD found in *Cannabis Indica* mitigate the anxiogenic effect of THC significantly. The effects of *Sativa* are well known for its cerebral high, hence it is often used during the day as medical *Cannabis*, while *Indica* is well known for its sedative effects and thus preferred at night time for medical *Cannabis* purposes. *Indica* plants are normally shorter and stockier plants than Sativas. They have wide, deeply serrated leaves and a compact and dense flower cluster.

Prior art cannabinoid products include U.S. Pat. No. 8,481,091 to Ross, which discloses an aerosol-based cannabinoid and U.S. Pat. No. 6,630,507 to Hampson et al., which teaches the use of cannabinoids as antioxidants and neuroprotectants. Further, published U.S. patent application Pub. No. US 2004/0049059 to Mueller discloses a method for producing an extract from cannabis plant matter, containing tetrahydrocannabinol and cannabidiol from ground dried cannabis plant matter that is subjected to a $CO_2$ extraction to obtain an extract.

THC is the primary psychoactive component of the *Cannabis* plant, and its concentration varies from species to species of *Cannabis*. Further, there are various methods of extracting THC from the *Cannabis* plant. However, there are no methods as yet to provide *Cannabis* infused coffee drinks with consistent amounts of THC. Thus, there is a need in the art for methods of making coffee products with consistent amount of THC.

SUMMARY

The present disclosure is directed to methods of making coffee products containing cannabinoids that are extracted from *Cannabis* plant. The innovative methods produce coffee products that possess the benefits of both coffee and the *Cannabis* plants. The methods can be used to produce different coffee products including, for example, single serve coffee pods, ground coffee, and espresso.

The disclosed methods for making coffee products include admixing cannabinoids into coffee products. In one embodiment, the method includes the steps of (a) extracting cannabinoids from *Cannabis* plant; and (b) admixing the cannabinoids into a coffee product.

Various methods for extracting cannabinoids from *Cannabis* plant are known in the art. Most methods include using a solvent, such as butane, hexane, isopropyl alcohol, ethanol, liquid carbon dioxide, and the like. According to an embodiment, the method for extracting the active cannabinoids from *Cannabis* plant includes the steps of (a) extracting cannabinoids using liquid carbon dioxide; (b) evaporating or purging liquid carbon dioxide; and (c) heating the cannabinoids at elevated temperature. According to another embodiment, isopropyl alcohol is used as a substitute for isopropyl alcohol. According to yet another embodiment, butane is used as a substitute for isopropyl alcohol.

There are different methods for admixing or infusing the cannabinoids into a coffee product. According to one embodiment, the cannabinoids can be admixed into a coffee product, for example, whole coffee beans or ground coffee beans, after cannabinoids was heated at elevated temperature. According to another preferred embodiment, the cannabinoids is first premixed with propylene glycol at elevated temperature to produce a homogenous mixture; the homogenous mixture is then admixed or infused into a coffee product.

There are different methods in producing a coffee product with consistent amount of THC. The amount of THC in a coffee product is controlled by the amount of the admixed or infused cannabinoids. According to one embodiment, the THC concentration in cannabinoids is analyzed by an analytical lab, and the result is used to control how much cannabinoids is required to provide the consistent amount of THC in a coffee product. According to another embodiment, by using same plant species, and by using liquid carbon dioxide to extract, the cannabinoids can be generated with consistent amount of THC, and consequently, producing a coffee product with consistent amount of THC without analyzing all the batches of cannabinoids.

The claimed method includes a coffee product with THC in a single-serve container that can be brewed to provide a consumable coffee drink that contains from about 5 mg to about 50 mg of THC.

Further, the claimed method includes a coffee product in a multi-serve container or can be used in a multiple serving coffee brewing unit to provide a consumable coffee drink that contains from about 5 mg to about 50 mg of THC.

These and other characteristics of the disclosed embodiments will become more apparent from the following description and illustrative embodiments which are described in detail with reference to the accompanying drawings.

BRIEF DESCRIPTION OF THE DRAWINGS

The drawings show a sample embodiment of a single-serve coffee infused with THC in accordance with the present invention, the details of which are explained below. In the drawings.

DETAILED DESCRIPTION

Figure 1:
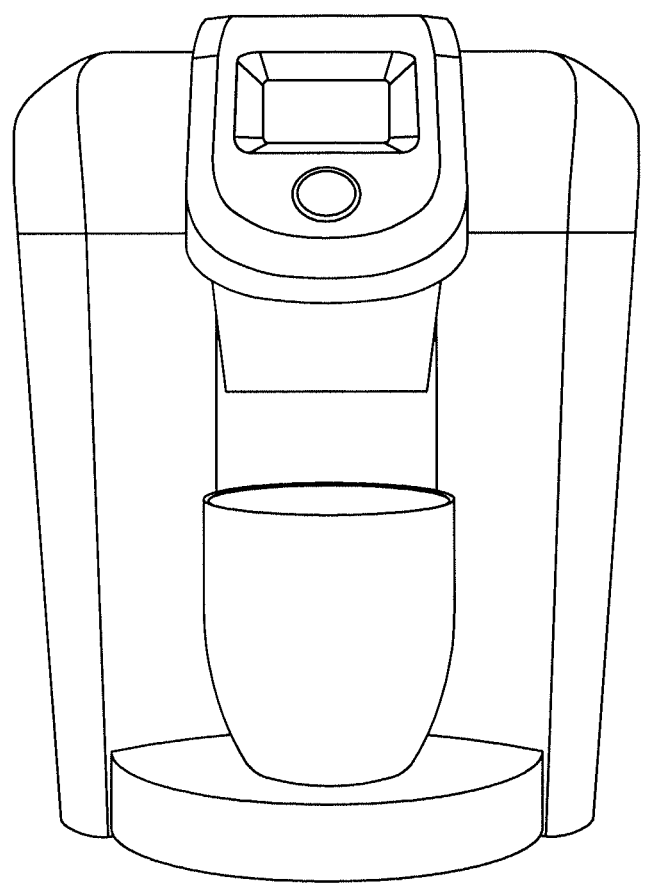
FIG. 1 is an illustration of a prior art brewer designed to brew a cup of coffee with a single-serve unit containing coffee grounds infused with THC.
Figure 2:
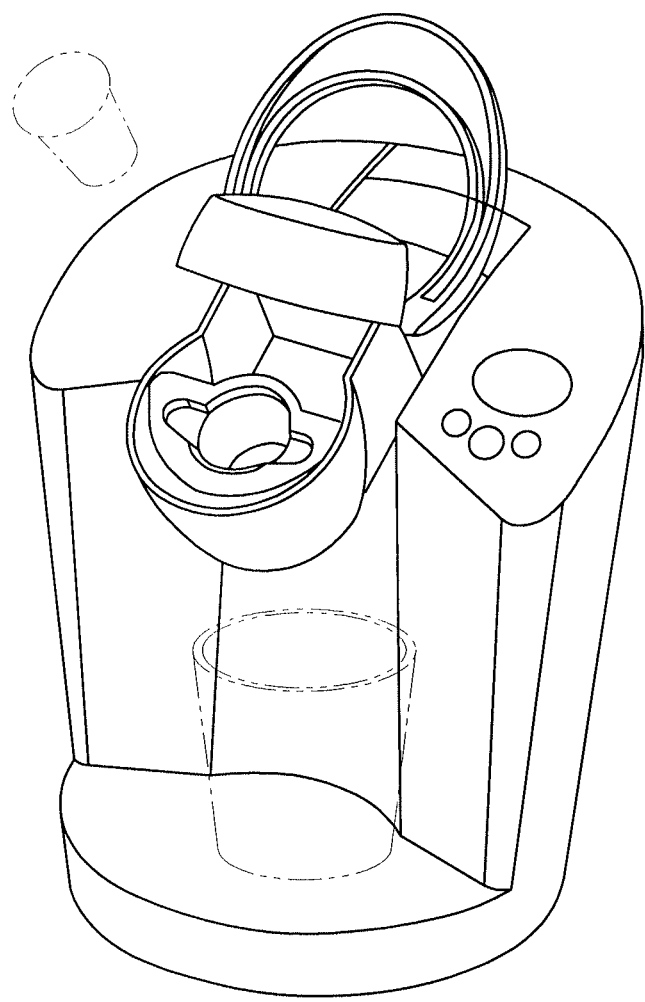
FIG. 2 is an illustration of a prior art brewer designed to brew a cup of coffee with a single-serve unit containing coffee grounds infused with THC.

The present disclosure is directed to inventive methods of making coffee products containing cannabinoids that are extracted from *Cannabis* plant. The disclosed method produces a coffee product that possesses the benefits of both coffee and the active ingredients of the *Cannabis* plant. The method can be used to produce different coffee products with desired and consistent amount of THC.

According to one embodiment of the invention the instantly claimed method can be used to produce a coffee product (with additional flavor if desired) with a consistent amount of THC using a coffee brewer for both home and commercial use. The coffee brewer can be any conventional coffee brewer that makes single or multiple cups of coffee. For example, the coffee product can be obtained by using a K-Cup®, i.e., a single-serving coffee brewing system. Wherein each K-Cup® is a plastic container with a coffee filter inside and ground coffee beans (flavored or unflavored) treated with a specific amount of THC packed together in the K-Cup® and sealed air-tight with a combination plastic and foil lid. When the K-Cup® is placed in an accommodating brewer, the brewer punctures both the foil lid and the bottom of the K-Cup® and forces hot water under pressure through the K-Cup® and into a cup to provide a consumable coffee drink containing a specified quantity of active cannabinoid compound(s). Further envisioned is the use of specific amounts of THC (and/or other cannabinoid compounds) not only for coffee, but K-Cup® varieties including http://en.wikipedia.org/wiki/Tea for example, tea, hot chocolate, iced tea, as well as fruit drinks.

The use of a K-Cup® or single-serve unit is not limited to the design of a K-Cup® and includes any single or multi-serve container or packaging which provides for the delivery of THC (and/or other cannabinoid compounds) with the consumable drink that can be processed by an accommodating brewing or mixing apparatus.

According to a specific embodiment of the invention, the method is directed to making coffee products containing cannabinoids that are extracted from *Cannabis* plant using single-use units that contain ground coffee and a specific quantity of THC in a propylene glycol solution, which then can be placed in an accommodating coffee brewing apparatus to provide a consumable coffee drink.

The presently claimed process envisions the use of various products, e.g., coffee, tea, hot chocolate and the like that include THC (and/or cannabinoid compounds) in single-use or multi-volume units that can be used with, for example single or multi brewing apparatus, with consumable fluids such as water (hot or cold), juice, milk, etc., to produce the desired consumable beverage.

Various systems for making and delivering individual and customized beverage product for a consumer are known in the art. U.S. Pat. Nos. 6,759,072, 7,438,941, 8,336,186, 8,586,117, and 8,720,320 disclose, inter alia, various liquid infusion and/or brewing processes, as well as various assemblies and containers (e.g., pods) to hold materials used to provide single-serve beverages. The entire contents of the references cited are incorporated herein by reference.

The disclosed method for making a coffee product includes the steps of extracting cannabinoids from *Cannabis* plant and admixing the cannabinoids into a coffee product.

There are different methods for extracting cannabinoids from the *Cannabis* plant. Most methods include using a solvent, such as butane, hexane, isopropyl alcohol, ethanol, and liquid carbon dioxide. Hash oil (also known as wax, nectar, full melt, honey, dabs, or budder) is a resinous matrix of cannabinoids obtained from the *Cannabis* plant by solvent extraction, formed into a hardened or viscous mass. According to an embodiment, the hash oil is made by passing liquid butane through a tube filled with *Cannabis* plant matter. The low temperature of the liquid butane crystallizes the *Cannabis* resins. As the butane passes through the tube the crystallized resins are trapped in the liquid butane. As the mixture of butane and resins exits the tube it is caught in a glass container. Butane is a volatile molecule and boils at $-1°$ C., leaving behind the resins only, which are collected from the glass container. This form is known as BHO or "Butane Hash Oil." After obtaining BHO in this method, BHO producers will then vacuum purge their oil in a vacuum chamber. The primary purpose of this step is to purge the butane still remaining trapped within the oil, because butane can have adverse health effects if inhaled. This "purging" process, depending on duration of exposure to vacuum and heat, will give the BHO characteristic textures, such as wax, crumble, shatter and budder. According to another embodiment, the hash oil is extracted using isopropyl alcohol.

According to yet another embodiment, the hash oil is extracted using liquid carbon dioxide, and this method is considered one of the most reliable and effective ways to produce cannabinoids with consistent amount of THC.

Most *Cannabis* plants are bred using both *Indica* and *Sativa*, which might provide inconsistent amount of THC upon extraction. However, it is considered desirable to extract cannabinoids from either *Indica* or *Sativa* plants to yield cannabinoids with consistent amount of THC.

After solvent extraction, the hash oil (i.e., extract) is heated to convert acid cannabinoids form to their neutral form, also called decarboxylation, while minimizing thermal degradation of THC to CBN. Decarboxylation of cannabinoid acids is a function of time and temperature, thus at higher temperatures a shorter period of time will be taken for complete decarboxylation of a given amount of cannabinoid acid. The temperature is generally in the range from $80°$ C. to $150°$ C., preferably in the range from $100°$ C. to $125°$ C. for a period of 30-60 minutes. According to an embodiment, the hash oil was heated at approximately $120°$ C. for a period of 30-45 minutes.

There are different methods for admixing the cannabinoids into a coffee product after carboxylation. For example, the cannabinoids can be admixed into a coffee product at elevated temperature. Alternatively, the cannabinoids is heated together with propylene glycol to yield a low viscosity mixture, and such mixture makes the admixing easier and more consistently than admixing the viscous cannabinoids directly. According to an embodiment, the cannabinoids and propylene glycol mixture is tested in a lab, and the amount of THC in a coffee product is controlled by adjusting the volume of the mixture based on the concentration of potency test results. Table 1 provides an example of the potency test results:

TABLE 1

Example of the cannabinoids potency test results
Potency Test Results

| Test | Weight % | Conc | Limit |
|---|---|---|---|
| CBD-V | <0.01% | <0.10 mg/g | N/A |
| CBD-A | <0.01% | <0.10 mg/g | N/A |
| CBG | 1.37% | 13.72 mg/g | N/A |
| CBD | 0.34% | 3.37 mg/g | N/A |
| THC-V | 0.21% | 2.08 mg/g | N/A |
| CBN | 0.80% | 8.04 mg/g | N/A |
| THC | 73.38% | 733.75 mg/g | N/A |
| CBC | 1.47% | 14.67 mg/g | N/A |
| THC-A | <0.01% | <0.10 mg/g | N/A |
| Max THC | 73.38% | 733.75 mg/g | N/A |
| Max CBD | 0.34% | 3.37 mg/g | N/A |
| Total Active | 77.56% | 775.64 mg/g | N/A |
| Total | 77.56% | 775.64 mg/g | N/A |

A coffee product can also be produced by infusing the cannabinoids into the product, e.g. coffee beans. Infusing is a process of one component permeating or penetrating into another component. Here, the cannabinoids is permeating into the coffee beans.

The Food and Drug Administration (FDA) has classified propylene glycol as "generally recognized as safe," which means that it is acceptable for use in flavorings, drugs, and cosmetics, and as a direct food additive. Therefore, propylene glycol to the extent necessary to dissolve the extracted cannabinoids can be in a final coffee product.

There are different methods in producing a coffee product with consistent amount of THC. The amount of THC in a coffee product is controlled by the amount of the admixed cannabinoids and its THC concentration. One method to obtain THC concentration is testing every batch of cannabinoids in an analytical lab. Alternatively, by using same plant species, and by using liquid carbon dioxide to extract, the cannabinoids can be generated with consistent amount of THC, and consequently, a single lab testing may be sufficient for different batches.

EXAMPLE 1 gram THC extracted via $CO_2$ extraction process from cannabis was mixed with about 3-4 ml propylene (an approximate 1:3 ratio)

THC is extracted via the above described $CO_2$ extraction process from cannabis 1 gram of the cannabis plant extract is mixed with about 3-4 ml of propylene glycol, which acts as a solvent. 7-10 drops of the extract and propylene glycol are mixed with 8-12 g of coffee grinds and place in a pod (e.g., K-Cup®) for use within a single serve coffee machine.

Similarly, about 7-12 ml of the cannabis plant extract and propylene glycol mixture recited supra is added to about one pound of coffee beans and allowed to stand for 24 hours. The coffee beans are then dried and ground for use in single serve units or large volume coffee brewing units (or commercial brewers). The quantity of THC is laboratory measured to provide uniform does within the single serve or multi volume coffee brewing devices.

The coffee can be treated with varying flavors.
Flavors including exemplary doses of THC:
CannaCafé Standard, known as CannaBliss: Standard Arabica coffee infused with *Sativa Cannabis* to provide a cognitive uplifting energetic feel; contains 80-100 mg caffeine and 20-25 mg of THC.

French Vanilla: *Sativa Cannabis* with French Vanilla flavoring added; contains 80-100 mg caffeine and 20-25 mg of THC.

Mocha: *Sativa Cannabis* with Mocha flavoring added; contains 80-100 mg caffeine and 20-25 mg of THC.

Caramel: *Sativa Cannabis* with Caramel flavoring added; contains 80-100 mg caffeine and 20-25 mg of THC.

Raging Bull: Higher caffeine dose of about the equivalent of a bold cup of coffee and espresso to provide a very energetic, uplifting head high, paired with *Sativa Cannabis*; contains 200-225 mg of caffeine and 65-70 mg of THC Focus: Highly Caffeinated coffee and *Sativa Cannabis* with a low level of THC; contains 175-220 mg of caffeine and 17-25 mg of THC.

Serenity: Decaffeinated coffee with a strong *Indica* based strain; contains 60-70 mg THC Yin Yang: Caffeinated coffee with a hybrid strain consisting of *Sativa* and *Indica*; contain 100 mg of caffeine and 30 mg of THC Other examples are directed to a formulation for a range of concentration of d9-tetrahydrocannabinol (THC) doses in a coffee K-cup as brewed on a Keurig® machine. The range being about 5 mg to about 25-50 mg, and in particular 10 mg concentration of d9-tetrahydrocannabinol (THC) dose in a coffee K-cup. The 50 mg THC dose is directed to a 'medicinal' K-cupd.

Increased solubility of THC in coffee was observed upon formulating a carbon dioxide ($CO_2$)—extracted THC oil with tapioca maltodextrin (TM).

The 10 mg dose was consistently achieved with 60% recovery from the aqueous phase, with the remainder of THC found to be deposited on the ceramic mug 20% or not recovered 20%. The medical preparation was found to have a low (~15%) yield and observed to produce TM chunks upon brewing.

THC is a highly lipophilic molecule with an aqueous solubility of 0.003 mg/mL, which amounts to 0.6 mg THC in a 200-mL cup (typical volume of a cup of coffee brewed on a Keurig®). The formulation of THC and TM improved solubility limitations and achieved the desired dosage levels of 10 and 50 mg of THC per cup of Keurig® brewed coffee.

The following factors were evaluated in this study: Solubility; Enhancement Optimum Ratio of THC Oil to TM; Uniformity of Dose; and Scalability.

The sourced raw $CO_2$ oil potency was measured at 21.1% THC. To 200 mg TM was added 39.8 mg of $CO_2$ oil and blended for roughly five minutes using a mortar and pestle for a 1:5 oil to TM ratio. 120 mg of the resultant mixture was taken and added to the top of 2039.8 mg coffee in a K-Cup. The cup was then sealed and brewed through the provided Keurig® machine. Three separate aliquots were taken from the resultant cup, C1 (top), C2 (middle), C3 (bottom) 0.5 mL from each sample was added to 0.5 mL of MeOH and centrifuged to remove solids. 0.5 mL of supernatant was then aliquoted into HPLC vials and assayed by HPLC-UV. The volume of the cup of coffee was measured to be 194 mL.

TABLE 1

Summary of THC Solubility Enhancement.

| Measurement | Top | Middle | Bottom |
|---|---|---|---|
| THC Input | 4.2 mg | 4.2 mg | 4.2 mg |
| THC Recovered | 0.8 mg | 0.8 mg | 0.8 mg |
| Recovery % | 19.1% | 19.1% | 19.1% |

The observed 0.8 mg of THC observed in the THC/TM formulation is not much better than the literature reported value of 0.6 mg of THC.

Due to this, an investigation of the used filter and coffee grounds was conducted. Extraction and subsequent HPLC-UV analysis of the used filter and coffee grounds found a substantial amount of THC being left behind in those matrices.

To avoid this loss of THC, the examples were performed by placing the THC/TM formulation beneath the filter in the K-cup.

Batches of $CO_2$ oil and TM were made using the method described in the 'Solubility' section to achieve ratios of 1:5, 1:10, and 1:15 (THC Oil:TM). Aliquots were taken out of the oil/TM mixes and dissolved separately into 10 mL of water and into 10 mL of coffee and assayed for THC concentration using HPLC-UV.

TABLE 2

Summary of 1:5, 1:10 and 1:15 $CO_2$/TM mixes.

| | Measurement | | | | | |
|---|---|---|---|---|---|---|
| | 1:5 water | 1:10 water | 1:15 water | 1:5 coffee | 1:10 coffee | 1:15 coffee |
| THC Concentration (mg/mL) | 0.060 | 0.048 | 0.067 | 0.160 | 0.563 | 0.578 |
| Theoretical mg of THC in 200 mL cup of coffee | 12.0 | 9.6 | 13.3 | 32.0 | 112.6 | 115.1 |

The 1:10 $CO_2$ oil/TM mix was deemed the best mix to use due a lack of increase in solubility being observed by increasing the TM ratio above 1:10.

The solubility of the THC/TM formulation was much higher in the coffee samples than in the water samples. This suggests that there are components within the coffee solution which significantly impact the solubility of the formulation.

This example investigated how THC was interacting with the coffee mug after it had been brewed. A cup of coffee was brewed with the 1:10 oil/TM mix placed in the K-Cup underneath the filter containing coffee grounds.

Two separate aliquots were taken from the cup (top and middle), and then coffee was carefully poured out. Methanol was added to the cup and the oil that had condensed to the sides of the cup was dissolved and quantified.

The sample taken from the top of the coffee cup was more concentrated in THC than a sample taken from the middle of the cup. This is consistent with the notion that the lipophilic THC molecule should selectively occupy an oily top layer of a cup of coffee.

TABLE 3

Summary of Coffee Mug Cross Section Analysis. Total THC input was 11.4 mg.

| Measurement | Top* | Middle* | Cup | Coffee Grounds and Filter | Unrecovered** |
|---|---|---|---|---|---|
| THC recovered | 7.4 mg | 6.4 mg | 2.4 mg | <0.1 mg | 2.2 mg |
| Recovery % | 64.9% | 56.2% | 21.1% | <0.1% | 19.3% |

*Recovery from Top and Middle of cup was extrapolated to a measurement of the full cup of coffee.
**Unrecovered calculation was based on an average of the Top and Middle recoveries.

Overall the vast majority of THC is making its way out of the K-cup and into the coffee mug. About 20% of the THC is binding to the sides of the ceramic coffee mug. About 20-25% of the THC is found in the oily coffee film at the top of the cup of coffee.

Under these conditions approximately 60% of the THC would be in the coffee, 20% would remain in the cup after drinking, and 20% is lost (unknown cause, most likely in the oily film floating at the top of the coffee, either consumed or not depending on user). Potential other pathways for loss would be determined in future experiments (chemical modification, volatilization, etc.).

To measure scalability, one 1:10 THC/TM mix was prepared as described above and its contents were analyzed in full. A four times larger preparation of 1:10 THC/TM mix was also prepared, and then divided into four different K-Cups to be processed and analyzed. The data obtained is presented below in Table 4.

TABLE 4

Assessment of the scalability of 1:10 THC/TM mix.

| Measurement | QC Cup | #2 | #3 | #4 | #5 |
|---|---|---|---|---|---|
| THC Input | 17.9 mg | 12.1 mg | 12.3 mg | 12.2 mg | 12.3 mg |
| THC Recovered | 7 mg | 6.8 mg | 7.2 mg | 7.0 mg | 7.6 mg |
| Recovery % | 39.1% | 56.2% | 58.5% | 57.4% | 61.8% |

The preparation scale-up did not negatively affect the THC recovery from coffee. To the contrary a small increase in recovery was observed in the larger scale preparation samples.

The relatively small relative standard deviation (RSD=4.8%) suggests that the K-cups can be expected to reliably produce a consistent dose of THC.

Additionally, a cup of coffee was brewed immediately after a THC-cup and did not contain any detectable amount of THC.

The description has not attempted to exhaustively enumerate all possible variations. That alternate embodiments may not have been presented for a specific portion of the invention, and may result from a different combination of described portions, or that other non-described alternate embodiments may be available for a portion, is not to be considered a disclaimer of those alternate embodiments. It will be appreciated that many of those non-described embodiments are within the literal scope of the following claims, and others are equivalent.

The invention claimed is:

1. A method for making a coffee product, comprising:
   (a) extracting cannabinoids using liquid carbon dioxide to yield a cannabis carbon dioxide extract containing cannabinoids;
   (b) evaporating or purging the carbon dioxide from the cannabis carbon dioxide extract containing cannabinoids;
   (c) heating the cannabis extract containing cannabinoids at an elevated temperature to yield a heated cannabis extract containing cannabinoids;
   (d) heating the extract containing cannabinoids with propylene glycol, or mixing the extract containing cannabinoids with maltodextrin to provide an extract containing cannabinoids and propylene glycol or maltodextrin; and
   (e) admixing the extract containing cannabinoids and propylene glycol or maltodextrin into coffee beans to provide said coffee product.

2. A method for making a coffee product, comprising:
   (a) extracting cannabinoids using liquid carbon dioxide to yield a cannabis carbon dioxide extract containing cannabinoids;
   (b) evaporating or purging the carbon dioxide from the cannabis carbon dioxide extract containing cannabinoids;
   (c) heating the cannabis extract containing cannabinoids at an elevated temperature to yield a heated cannabis extract containing cannabinoids;
   (d) heating the extract containing cannabinoids with propylene glycol, or mixing the extract containing cannabinoids with maltodextrin to yield an extract containing cannabinoids and propylene glycol or maltodextrin; and
   (e) infusing the extract containing cannabinoids and propylene glycol or maltodextrin into coffee beans mixture into a to provide said coffee product.

3. A method for making a coffee product, comprising:
   (a) extracting cannabinoids from cannabis using butane to yield a cannabis butane extract containing cannabinoids;
   (b) evaporating or purging the butane from the cannabis butane extract containing cannabinoids;
   (c) heating the cannabis extract containing cannabinoids at an elevated temperature to yield a heated cannabis extract containing cannabinoids; and
   (d) admixing the heated cannabis extract containing cannabinoids into coffee beans to yield said coffee product.

4. The method according to claim 3, wherein step (c) heating is at a temperature from about 80° C. to about 150° C.

5. The method according to claim 3, wherein step (c) heating is at a temperature from 100° C. to 125° C.

6. The method according to claim 3, wherein said elevated temperature is approximately 120° C., and the cannabinoids are heated for 30-45 minutes at this temperature.

7. The method according to claim 3, wherein said admixing the cannabinoids into a coffee product further comprising:
   (a) heating the cannabinoids with propylene glycol to provide a mixture containing cannabinoids and propylene glycol; and
   (b) admixing or infusing the mixture containing cannabinoids and propylene glycol mixture to provide the coffee product.

8. The method according to claim 3, wherein said coffee product is a coffee pod.

9. The method according to claim 3, wherein said admixing the cannabinoids into a coffee product further comprising:
   (a) analyzing cannabinoids;
   (b) calculating the concentration of THC in the cannabinoids; and
   (c) adjusting the amount of cannabinoids based on the concentration of THC.

10. The method according to claim 7, wherein said admixing the cannabinoids and propylene glycol mixture into a coffee product further comprising:
    (a) analyzing cannabinoids;
    (b) calculating the concentration of THC in the mixture containing cannabinoids and propylene glycol; and
    (c) adjusting the amount of cannabinoids and propylene glycol based on the concentration of THC.

11. The method according to claim 3, wherein said coffee product contains from about 1 mg to about 100 mg of THC.

12. The method according to claim 3, wherein said coffee product contains from about 5 mg to about 50 mg of THC.

13. The method according to claim 3, wherein said coffee product contains from about 10 mg to about 30 mg of THC.

14. The method according to claim 3, wherein said coffee product is in a single-serve container that can be brewed to provide a consumable coffee drink that contains from about 5 mg to about 50 mg of THC.

15. The method according to claim 3, wherein said coffee product is in a multi-serve container that can be brewed to provide a consumable coffee drink that contains from about 5 mg to about 50 mg of THC.

16. A method for making a coffee product, comprising:
    (a) extracting cannabinoids from cannabis using isopropyl alcohol to yield a cannabis isopropyl alcohol extract containing cannabinoids;
    (b) evaporating or purging the isopropyl alcohol from the cannabis isopropyl alcohol extract containing cannabinoids;
    (c) heating the cannabis extract containing cannabinoids at an elevated temperature to yield a heated cannabis extract containing cannabinoids;
    (d) mixing the extract containing cannabinoids with maltodextrin to provide an extract containing cannabinoids and maltodextrin; and
    (e) admixing the extract containing cannabinoids and maltodextrin into coffee beans to provide said coffee product.

17. The method according to claim 1, wherein said coffee product is a coffee pod.

18. The method according to claim 2, wherein said coffee product is a coffee pod.

* * * * *